(12) United States Patent
Thanki et al.

(10) Patent No.: US 6,307,055 B1
(45) Date of Patent: Oct. 23, 2001

(54) DIOL-FUNCTIONALIZED UV ABSORBER

(75) Inventors: Paragkumar Nathalal Thanki; Raj Pal Singh, both of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/749,266

(22) Filed: Dec. 27, 2000

(51) Int. Cl.$^7$ .................................................. C07D 249/20
(52) U.S. Cl. ........................................... 548/259; 548/260
(58) Field of Search ..................................... 548/259, 260

(56) References Cited

U.S. PATENT DOCUMENTS 5,459,222 * 10/1995 Rodgers et al. ........................ 528/73

* cited by examiner

*Primary Examiner*—Patricia L. Morris
(74) *Attorney, Agent, or Firm*—Ladas & Parry

(57) ABSTRACT

The invention pertains to novel UV absorbing diol of the general formula:

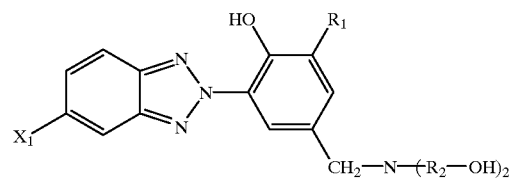

wherein $R_1$ is hydrogen, tert-butyl; $X_1$ is selected the group consisting of hydrogen, halogen, tert-butyl and $C_1$ to $C_{12}$ alkoxy; $R_2$ is $C_1$ to $C_8$ linear or branched alkyl, and to a process for the preparation thereof.

1 Claim, No Drawings

DIOL-FUNCTIONALIZED UV ABSORBER

FIELD OF THE INVENTION

The present invention relates to novel diol functionalised UV absorbers. More particularly it relates to the said absorbers having a general formula 1

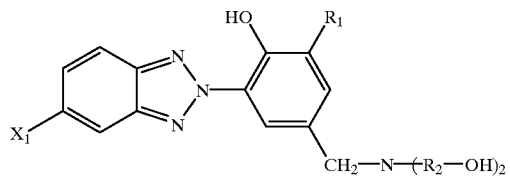

Formula 1 where $R_1$ is hydrogen or tert-butyl; $X_1$ is selected the group consisting of hydrogen, halogen, tert-butyl and $C_1$ to $C_{12}$ alkoxy; $R_2$ is $C_1$ to $C_8$ linear or branched alkyl Still more particularly, the invention concerns the synthesis of diol derivatives of conventional UV absorbers useful as condensable monomers for the synthesis of many polymers with in-built UV absorbers.

Our copending application Ser. No. 09/749,276 filed on the same day as this application relates to a process for the preparation of the novel diol functionalised absorbers of the general formula 1.

BACKGROUND OF THE INVENTION

Diol containing pendant UV absorbing groups are gaining much more importance to stabilize the polyurethane and polyesters against photochemical degradation. Eur. Pat. No. 627452 A1 and 627452 B1 disclose the preparation of diols with pendant UV absorbing moiety and also the preparation of polyurethane and polyesters from diols containing pendant UV absorbing groups. One class of diols disclosed in the above referred European patents is of the general formula 2 below:

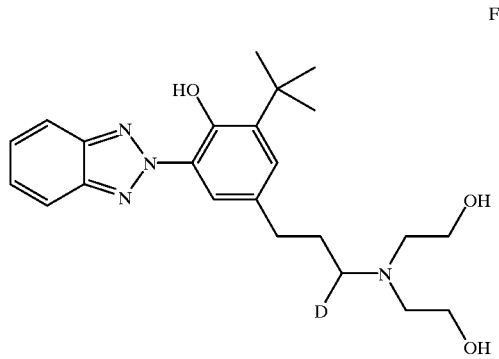

Formula 2

This particular class of diols have an amide group present within their molecule, which could be susceptible to hydrolysis. Moreover, the diols disclosed herein bear tertiary amine linkage, which is known for its ability to quench singlet oxygen and make substrate stable towards oxidative degradation.

Eur. Pat. No. 627452 A1 and 627452 B1 also disclose another class of diols of the general formula 3 below:

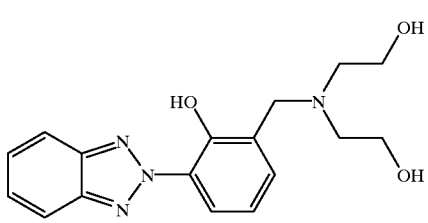

Formula 3

This particular class of diols were prepared by Manioh reaction with total time duration of 24 h. Whereas the process for the preparation of the diols disclosed herein is much faster having the total preparation time duration of 12 h.

Most thermoplastic polymers and coating compositions are unstable to the extended exposure to ultraviolet light source in atmosphere. Thermoplastics and coatings tend to demonstrate unwanted colour changes and reduced mechanical strength upon exposure to UV radiation. The preliminary effect of ultraviolet radiation on polymers is the formation of free radicals on the polymer chain, which react with atmospheric oxygen. This results in the formation of peroxide groups. Furthermore, decomposition of peroxide groups causes formation of carbonyl groups and chain scission. Irradiation in absence of oxygen causes the increase in crosslinking. Ultimately, this reflects on the mechanical properties and the colour of the polymeric materials. In order to prevent or at least retard the damage caused by these factors, stabilizers are added to the plastics.

UV absorbers are compounds which on addition to the polymers are capable of preventing or retarding the degradation reactions caused by light energy. 2-Hydroxyphenyl benzotriazoles are the one of the most important UV absorbers, which are used commercially. The preparation and use of functional UV absorber in polymers and coatings is well documented in the art.

The utility of monomeric and low molecular weight UV absorbers is limited due to their properties of migration and leaching. This phenomenon could lead to uneven distribution of UV absorbers within the polymeric matrix. Leaching could be even more harmful as the loss of UV absorbers from the polymer matrix could lead to extensive photodegradation of the substrate. Therefore, in order to prevent the phenomena of migration and leaching, the UV absorbers with polymerizing ability are being developed This particular class of stabilizers would have even distribution within the polymer matrix and also they overcome the phenomena of migration and leaching.

OBJECTS OF THE INVENTION

The main object of the present invention is to provide a novel diol functionalized UV absorber.

It is another object of the invention to provide a novel diol functionalised UV absorber which has even distribution within the polymer matrix and wherein the phenomena of migration and leaching are overcome or minimised.

SUMMARY OF THE INVENTION

Accordingly the present invention provides novel diol functionalized UV absorber having the general formula 1

Formula 1

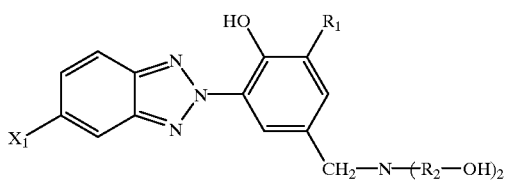

wherein $R_1$ is hydrogen, tert-butyl; $X_1$ is selected the group consisting of hydrogen, halogen, tert-butyl and $C_1$ to $C_{12}$ alkoxy; $R_2$ is $C_1$ to $C_8$ linear or branched alkyl.

The present invention also relates to a process for the preparation of novel diol functionalised UV absorbers of the general formula 1 below Formula 1

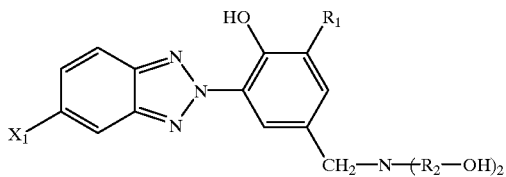

which comprises reacting novel bromo-functionalized benzotriazole UV absorber having the general formula 4

Formula 4

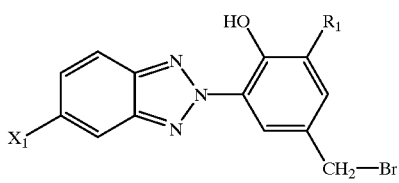

wherein $R_1$ is hydrogen or tert-butyl; $X_1$ is selected the group consisting of hydrogen, halogen, tert-butyl and $C_1$ to $C_{12}$ alkoxy, with diethanol diamine in an organic solvent under reflux at a temperature in the range of 70 to 90° C. for a time period ranging from 5–8 hrs, removing the solvent and recrystallizing the resultant compound to obtain the desired pure compound.

In one embodiment of the present the organic solvent used is acetone.

DETAILED DESCRIPTION OF THE INVENTION

The following examples describe the process for the preparation of the diol which are illustrative only and should not be construed to the scope of the scope of the present invention in any manner.

EXAMPLE 1

Synthesis of 2-(2'-Hydroxy-5'-bromomethylphenyl) benzotriazole 2-(2'-Hydroxy-5'-bromomethylphenyl)benzotriazole was prepared from the bromination of 2-(2'-Hydroxy-5'-methylphenyl)benzotriazole using azobis isobutyronitrile (AIBN) as an initiator. In a 500 ml three-necked round bottomed flask, 5 g (0.0223 mol) of 2-(2'-Hydroxy-5'-methylphenyl)benzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2(2'Hydroxy5'-methylphenyl) benzotriazole was kept in oil-bath with temperature 47° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-Hydroxy-5'-bromomethylphenyl) benzotriazole was 5.5 g (80%)

EXAMPLE 2

Synthesis of 2-(2'-Hydroxy-3'-tert-butyl-5'-bromomethylphenyl)-5-chlorobenzotriazole 2-(2'-Hydroxy-3'-tert-butyl-5'-bromomethylphenyl)-5-chlorobenzotriazole was prepared from the bromination of 2-(2'-Hydroxy-3'-tert-butyl-5'-methylphenyl)-5-chlorobenzotriazole using azobis isobutyronitrile (AIBN) as an initiator. In a 500 ml three-necked round bottomed flask, 7.042 g (0.0223 mole) 2-(2'-Hydroxy-3'-tert-butyl-5'-methylphenyl)-5-chlorobenzotriazole and 100 mg of AIBN were taken and dissolved in 150 ml of dry carbon tetrachloride. In a separate conical flask 4.18 g (1.5 ml, 0.03 mole) of bromine was dissolved in 75 ml of dry carbon tetrachloride and solution was transferred to a cylindrical funnel with pressure equalizing tube. Three-necked round-bottomed flask containing solution of 2-(2'-Hydroxy-3'-tert-butyl-5'-methylphenyl)-5-chlorobenzotriazole was kept in oil-bath with temperature 50° C. Nitrogen was bubbled through the solution for creating inert atmosphere Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature Product was separated by solvent evaporation. Finally the product was purified by recrystallization from acetone. The yield of 2-(2'-Hydroxy-3'-tert-butyl-5'-bromomethylphenyl)-5-chlorobenzotriazole was 7.2 g (81%).

EXAMPLE 3

Synthesis of 2-(2'-hydroxy-3'-tert-butyl-5'-bromomethyphenyl)benzotriazole 2-(2'-hydroxy-3'-tert-butyl-5'-bromomethyphenyl) benzotriazole was prepared from the bromination of 2-(2'-hydroxy-3'-tert-butyl-5'-methyphenyl)benzotriazole using azobis isobutyronitrile (AIBN) as an initiator. In a 500 ml three-necked round bottomed flask, 6.274 g (0.0223 mol) 2-(2'-hydroxy-3'-tert-butyl-5'-methyphenyl)benzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-3'-tert-butyl-5'-methylphenyl)benzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-3'-tert-butyl-5'-bromomethyphenyl) benzotriazole was 6.6 g (82%)

EXAMPLE 4

Synthesis of 2-(2'-hydroxy-5'-bromomethyphenyl)-5-tert-butylbenzotriazole

2(2'hydroxy 5'-bromomethyphenyl)-5-tert-butylbenzotriazole was prepared from the bromination of 2-(2'-hydroxy-5'-methyphenyl)-5-tert-butylbenzotriazole using azobis isobutyronitrile (AIBN) as an initiator. In a 500 ml three-necked round bottomed flask, 6.274 g (0.0223 mol) 2-(2'-hydroxy-5'-methyphenyl)-5-tert-butylbenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-tert-butylbenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-tert-butylbenzotriazole was 6.8 g (84%)

EXAMPLE 5

Synthesis of 2-(2'-hydroxy-5'-bromomethyphenyl)-5-ethoxy benzotriazole 2-(2'-hydroxy-5'-bromomethyphenyl)-5-ethoxybenzotriazole was prepared from the bromination of 2-(2'-hydroxy-5'-methyphenyl)-5-ethoxybenzotriazole using azobis isobutyronitrile (AIBN) as an initiator. In a 500 ml three-necked round bottomed flask, 6.275 g (0.0223 mol) 2-(2'-hydroxy-5'-methyphenyl)-5-ethoxybenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round bottomed flask containing solution of 2-(2'-hydroxy-5'-methyphenyl)-5-ethoxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Produce was separated by solvent evaporation Finally the product was purified by recrystallization from acetone. The yield of 2-(2'-hydroxy-5'-bromomethyphenyl)-5-ethoxybenzotriazole was 6.6 g (85%)

EXAMPLE 6

Synthesis of 2-(2'-hydroxy-5'-bromomethyphenyl)-5-tert-octyloxybenzotriazole 2-(2'-hydroxy-5'-bromomethyphenyl)-5-tert-octyloxybenzotriazole was prepared from the bromination of 2-(2'-hydroxy-5'-methyphenyl)-5-tert-octyloxybenzotriazole using azobis isobutyronitrile (AIBN) as an initiator. In a 500 ml three-necked round bottomed flask, 8.236 g (0.0223 mol) 2-(2'-hydroxy-5'-methyphenyl)-5-tert-octyloxybenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2 (2'hydroxy 5'methyphenyl)-5-tert-octyloxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-tert-octyloxybenzotriazole was 7.8 g (81%).

EXAMPLE 7

Synthesis of 2-(2'-hydroxy-5'-bromomethyphenyl)-5-methoxybenzotriazole 2-(2'-hydroxy-5'-bromomethyphenyl)-5-methoxybenzotriazole was prepared from the bromination of 2-(2'-hydroxy-5'-methyphenyl)-5-methoxybenzotriazole using azobis isobutyronitrile (AIBN) as an initiator. In a 500 ml three-necked round bottomed flask, 5.693 g (0.0223 mol) 2-(2'-hydroxy-5'-methyphenyl)-5-methoxybenzotriazole and 100 mg of AIBN were taken and dissolved in 150 ml of dry carbon tetrachloride. In a separate conical flask 4.18 g (1.5 ml, 0.03 mol) of bromine was dissolved in 75 ml of dry carbon tetrachloride and solution was transferred to a cylindrical funnel with pressure equalizing tube. Three-necked round-bottomed flask containing solution of 2-(2'-hydroxy-5'-methyphenyl)-5-methoxybenzotriazole was kept in oil-bath with temperature 50° C. Nitrogen was bubbled through the solution for creating inert atmosphere. Cylindrical funnel containing bromine solution was mounted on the three-necked round-bottomed flask. Solution in the flask was continuously stirred with the help of magnet stirrer. Bromine solution was added, drop-by-drop, from funnel to the flask for a span of 4–5 hours till all the solution was poured out. After that heating was stopped and the final reaction mixture was allowed to cool at room temperature. Product was separated by solvent evaporation. Finally the product was purified by recrystallization from acetone. The yield of 2-(2'-hydroxy-5'-bromomethyphenyl)-5-methoxybenzotriazole was 6.3 g (84%).

EXAMPLE 8

Synthesis of 2-(2'-Hydroxy-5'-(bis(2-hydroxyethyl) aminomethyl) phenyl) benzotriazole 2-(2'-Hydroxy-5'bromomethylphenyl)benzotriazole (3.03 g. 0.01 mole), diethanol amine (3.14 g. 0.03 mole) were dissolved in 100 ml. of acetone. The reaction mixture was refluxed with constant stirring at 75° C. for 6 h. The solvent was then removed by rotary evaporation. Crude product was purified using silica gel column chromatography Product was identified by $^1$H-NMR.

EXAMPLE 9

Synthesis of 2-(2'-Hydroxy-3'-tert-butyl-5'-(bis (2-hydroxyethyl) aminomethyl) phenyl)-5-chlorobenzotriazole 2-(2'-Hydroxy-3'-tert-butyl-5'-methylphenyl)-5-chlorobenzotriazole (3.95 g. 0.01 mole), diethanol amine (3.14 g 0.03 mole) was dissolved in 100 ml. of acetone The reaction mixture was refluxed with constant stirring at 80° C. for 6 h. The solvent was then removed by rotary evaporation. Crude product was purified using silica gel column chromatography. Product was identified by $^1$H-NMR.

We claim:

1. Diol functionalized UV absorbers having the general formula 1

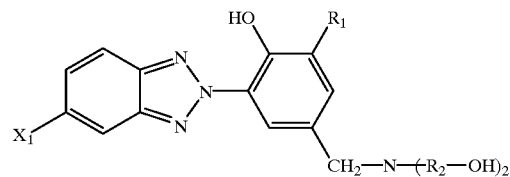

Formula 1 where $R_1$ is hydrogen, tert butyl; $X_1$ is selected the group consisting of hydrogen, halogen, tert-butyl and $C_1$ to $C_{12}$ alkoxy; $R_2$ is $C_1$ to $C_8$ linear or branched alkyl.

* * * * *